United States Patent
Itu et al.

(10) Patent No.: US 10,758,125 B2
(45) Date of Patent: Sep. 1, 2020

(54) ENHANCED PERSONALIZED EVALUATION OF CORONARY ARTERY DISEASE USING AN INTEGRATION OF MULTIPLE MEDICAL IMAGING TECHNIQUES

(71) Applicant: Siemens Healthcare GmbH, Erlangen (DE)

(72) Inventors: Lucian Mihai Itu, Brasov (RO); Tiziano Passerini, Plainsboro, NJ (US); Saikiran Rapaka, Pennington, NJ (US); Puneet Sharma, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 113 days.

(21) Appl. No.: 16/081,042

(22) PCT Filed: Apr. 28, 2017

(86) PCT No.: PCT/IB2017/000634
§ 371 (c)(1),
(2) Date: Aug. 30, 2018

(87) PCT Pub. No.: WO2017/187269
PCT Pub. Date: Nov. 2, 2017

(65) Prior Publication Data
US 2019/0029519 A1    Jan. 31, 2019

Related U.S. Application Data

(60) Provisional application No. 62/329,539, filed on Apr. 29, 2016.

(51) Int. Cl.
*A61B 5/00* (2006.01)
*A61B 5/02* (2006.01)
(Continued)

(52) U.S. Cl.
CPC .......... *A61B 5/0035* (2013.01); *A61B 5/0044* (2013.01); *A61B 5/02007* (2013.01);
(Continued)

(58) Field of Classification Search
None
See application file for complete search history.

(56) References Cited

U.S. PATENT DOCUMENTS 9,349,178 B1    5/2016 Itu et al.
2011/0164035 A1*    7/2011 Liao .................... G06T 7/246
345/419

(Continued)

FOREIGN PATENT DOCUMENTS

WO    WO2015150128 A1    10/2015

OTHER PUBLICATIONS

International Search Report dated Sep. 15, 2017 in corresponding International Application No. PCT/IB2017/000634.
(Continued)

*Primary Examiner* — Leon Viet Q Nguyen

(57) ABSTRACT

A method for providing a personalized evaluation of CAD for a patient includes acquiring one or more non-invasive images depicting a patient's coronary arteries and extracting a first set of features of interest from the one or more non-invasive images. A machine learning model is applied to the first set of features of interest to yield a prediction of one or more coronary measures of interest. One or more invasive images depicting the patient's coronary arteries are acquired and a second set of features of interest are extracted from the one or more invasive images. The first set of features of interest and the second set of features of interest are combined to yield a combined set of features of interest. Then, the machine learning model may be applied to the
(Continued)

combined set of features of interest to yield an enhanced prediction of the coronary measures of interest.

18 Claims, 10 Drawing Sheets

(51) Int. Cl.
| | |
|---|---|
| *A61B 6/00* | (2006.01) |
| *A61B 8/08* | (2006.01) |
| *G16H 40/20* | (2018.01) |
| *A61B 6/03* | (2006.01) |
| *G16H 50/50* | (2018.01) |
| *G16H 50/20* | (2018.01) |
| *A61B 5/026* | (2006.01) |

(52) U.S. Cl.
CPC .......... *A61B 5/7221* (2013.01); *A61B 5/7267* (2013.01); *A61B 5/743* (2013.01); *A61B 6/032* (2013.01); *A61B 6/504* (2013.01); *A61B 6/5217* (2013.01); *A61B 8/0891* (2013.01); *G16H 40/20* (2018.01); *G16H 50/20* (2018.01); *G16H 50/50* (2018.01); *A61B 5/0073* (2013.01); *A61B 5/026* (2013.01); *A61B 5/7275* (2013.01); *A61B 5/7282* (2013.01); *A61B 6/503* (2013.01); *A61B 6/507* (2013.01); *A61B 6/5247* (2013.01); *A61B 8/0883* (2013.01); *A61B 8/5223* (2013.01); *A61B 8/5261* (2013.01); *A61B 2576/023* (2013.01)

(56) References Cited

U.S. PATENT DOCUMENTS

| | | | |
|---|---|---|---|
| 2012/0004537 | A1 | 1/2012 | Tolkowsky et al. |
| 2014/0073976 | A1 | 3/2014 | Fonte et al. |
| 2015/0112182 | A1* | 4/2015 | Sharma ................ A61B 6/5217 600/408 |
| 2017/0132388 | A1* | 5/2017 | Grady .................... G16H 50/50 |
| 2017/0245824 | A1* | 8/2017 | Schmitt .............. A61B 5/02007 |

OTHER PUBLICATIONS

Bishop CM. Pattern recognition and machine learning. New York, NY: Springer, 2006.

Coenen A, Lubbers MM, Kurata A, Kono A, Dedic A, Chelu RG, Dijkshoorn ML, Gijsen FJ, Ouhlous M, van Geuns RJM, Nieman K. Fractional flow reserve computed from noninvasive CT angiography data: diagnostic performance of an on-site clinician-operated computational fluid dynamics algorithm. Radiology 274: 674-683, 2015.

Renker et al., Comparison of Diagnostic Value of a Novel Noninvasive Coronary Computed Tomography Angiography Method versus Standard Coronary Angiography for Assessing Fractional Flow Reserve, Am J Cardiol, vol. 114, pp. 1303-1308, 2014.

Koo et al., "Diagnosis of Ischemia-Causing Coronary Stenoses by Noninvasive Fractional Flow Reserve Computed from Coronary Computed Tomographic Angiograms", J Am Coll Cardiol, vol. 58, pp. 1989-1997, 2011.

Lim, Woo-Hyun, et al. "Variability of Fractional Flow Reserve According to the Various Methods to Induce Hyperemia." Journal of the American College of Cardiology 63.12 Supplement (2014): A1766.

Min et al., Diagnostic Accuracy of Fractional Flow Reserve from Anatomic CT Angiography, JAMA, vol. 308, pp. 1237-1245, 2012.

Morris et al., "Virtual Fractional Flow Reserve from Coronary Angiography: Modeling the Significance of Coronary Lesions", J Am Coll Cardiol Intv, vol. 6, pp. 149-157, 2013.

Nørgaard, Bjarne L., et al. "Diagnostic performance of noninvasive fractional flow reserve derived from coronary computed tomography angiography in suspected coronary artery disease: the NXT trial (Analysis of Coronary Blood Flow Using CT Angiography: Next Steps)." Journal of the American College of Cardiology 63.12 (2014): 1145-1155.

M. I. Papafaklis, MD. et al., "Fast virtual functional assessment of intermediate coronary lesions using routine angiographic data and blood flow simulation in humans: comparison with pressure wire—fractional flow reserve," EuroIntervention, pp. 1-14, 2014.

N. Pijls and B. De Bruyne, Coronary Pressure. Springer 2000.

Shaw, Leslee J., et al. "Coronary computed tomographic angiography as a gatekeeper to invasive diagnostic and surgical procedures: results from the multicenter CONFIRM (Coronary CT Angiography Evaluation for Clinical Outcomes: an International Multicenter) registry." Journal of the American College of Cardiology 60.20 (2012): 2103-2114.

Taylor CH. A. et al; "Computational Fluid Dynamics Applied to Cardiac Computed Tomography for Noninvasive Quantification of Fractional Flow Reserve—Scientific Basis"; Journal of the American College of Cardiology (JACC); vol. 61; No. 22; pp. 2233-2241.

S. Tu, PhD et al., "Fractional Flow Reserve Calculation From 3-Dimensional Quantitative Coronary Angiography and TIMI Frame Count," JACC: Cardiovasular Interventions, vol. 7, No. 7, pp. 768-777, 2014.

* cited by examiner

|  | | XA-FFR | |
|---|---|---|---|
|  | | Neg | Pos |
| CCTA-FFR | Neg | Lesion is negative (XA is not performed) | Lesion is considered positive or invasive measurement may be performed if measure of interest is positive but close to the threshold value |
|  | Pos | Lesion is negative: XA based prediction has higher confidence since it also integrates CCTA information and the CCTA threshold may also be biased towards negative lesions | Lesion is positive |

Fig. 8

ENHANCED PERSONALIZED EVALUATION OF CORONARY ARTERY DISEASE USING AN INTEGRATION OF MULTIPLE MEDICAL IMAGING TECHNIQUES

CROSS-REFERENCE TO RELATED APPLICATIONS

This application claims the benefit of U.S. Provisional Application Ser. No. 62/329,539 filed Apr. 29, 2016, which is incorporated herein by reference in its entirety.

TECHNICAL FIELD

The present invention relates generally to methods, systems, and apparatuses for the personalized evaluation of coronary artery disease using non-invasive and invasive medical imaging techniques.

BACKGROUND

The decision to revascularize blocked coronaries is commonly performed considering anatomical markers extracted from invasive coronary angiography, such as the percentage reduction in lumen diameter. Subjective assessment of angiographically apparent Coronary Artery Disease (CAD) is inadequate due to high degrees of intra-observer and inter-observer variability. Hence, the significance of coronary stenosis is routinely assessed by computer-assisted quantitative coronary angiography. There is strong evidence that this approach has a limited accuracy in evaluating the hemodynamic significance of lesions. In view of the limitations of the pure anatomical evaluation of CAD, the functional index of Fractional Flow Reserve (FFR) has been introduced as an alternative.

Currently, invasively measured FFR is the "gold standard" to determine lesion-specific ischemia, but it has some limitations. The requirement to introduce a wire into the coronary arteries is a potential source of complications, and adverse effects can also be caused by adenosine medication. Furthermore, the logistical effort and financial expense pose a relevant limitation in clinical practice.

Recently, blood flow computations performed using computational fluid dynamics (CFD) algorithms in conjunction with patient-specific anatomical models extracted from medical images (e.g., CT or angiography based scans of the heart and the coronary arteries) have shown great promise in being able to predict invasive, lesion-specific FFR from patient's medical images taken at resting conditions. The CFD-based models combine geometrical information extracted from medical imaging with background knowledge on the physiology of the system, encoded in a complex mathematical fluid flow model comprising partial differential equations which can be solved only numerically. This approach leads to a large number of algebraic equations, making it computationally very demanding.

The computationally demanding aspect of these CFD models and associated image segmentation process prevents adoption of this technology for real-time applications such as intra-operative guidance of interventions. An alternative approach with high predictive power is based on machine learning (ML) algorithms. In this case, the relationship between input data, such as the anatomy of a vascular tree and quantities of interest (e.g., FFR) is represented by a model built from a database of samples with known characteristics and outcome. Once the model is trained, its application to unseen data provides results almost instantaneously.

Previous approaches, both based on CFD and on ML focus on a single imaging modality, either Coronary Computed Tomography Angiography (CCTA) or X-ray Angiography (XA). In many clinical workflows first non-invasive imagining is followed by invasive imaging in case there is an indication for a functionally significant lesion.

SUMMARY

Embodiments of the present invention address and overcome one or more of the above shortcomings and drawbacks by providing methods, systems, and apparatuses related to combining information from non-invasive and invasive medical images of Coronary Artery Disease (CAD) patients.

According to some embodiments, a method for providing a personalized evaluation of coronary artery disease (CAD) for a patient includes acquiring non-invasive images depicting a patient's coronary arteries (e.g., CCTA images) and extracting a first set of features of interest from the non-invasive images. A machine learning model is applied to the first set of features of interest to yield a prediction of coronary measures of interest. These coronary measures of interest may include, for example, a measurement of Fractional Flow Reserve (FFR), a measurement of instantaneous wave-free ratio (IFR), ratio of resting distal pressure to aortic pressure (rest Pd/Pa), basal stenosis resistance (BSR), hyperemic stenosis resistance (HSR), and index of microcirculatory resistance (IMR). Invasive images depicting the patient's coronary arteries (e.g., XA images) are acquired and a second set of features of interest are extracted from the invasive images. The first set of features of interest and the second set of features of interest are combined to yield a combined set of features of interest. Then, the machine learning model may be applied to the combined set of features of interest to yield an enhanced prediction of the coronary measures of interest.

The aforementioned method may be modified or refined to provide additional features in different embodiments of the present invention. For example, in some embodiments, the combined set of features of interest further includes the prediction of the coronary measures of interest. In some embodiments, the features are extracted directly from the non-invasive images. The method may further include generating a geometric model of the patient's coronary arteries using the non-invasive images. The features may then be extracted from the geometric model.

Some embodiments of the aforementioned method further include determining whether the enhanced prediction of the coronary measures of interest is in a gray zone of a hybrid decision making strategy. This hybrid decision making strategy may be based, for example, on a decision of performing iFR measurements or FFR measurements. If the coronary measures of interest are in the gray zone of the hybrid decision making strategy, an invasive measurement of the coronary measures of interest may be performed to acquire invasive measurement data. The machine learning model may be retrained based on the invasive measurement data and the combined set of features of interest.

According to another aspect of the present invention, a second computer-implemented method for providing a personalized evaluation of CAD for a patient includes acquiring non-invasive images depicting a patient's coronary arteries and extracting a first set of features of interest from the non-invasive images. A machine learning model is applied to the first set of features of interest to yield a prediction of coronary measures of interest. Invasive images depicting the patient's coronary arteries are acquired and a second set of features of interest are extracted from the invasive images. Then, either (i) a correction of at least a portion of the first set of features of interest is performed using the second set of features of interest or (ii) a correction of at least a portion of the second set of features of interest is performed using the first set of features of interest to yield a corrected set of features of interest.

In some embodiments of the aforementioned second method, an invasive measurement of the coronary measures of interest is acquired and additional corrections on the corrected set of features of interest are performed based on the invasive measurement. The machine learning model may be applied to the corrected set of features of interest to yield an updated prediction of the coronary measures of interest.

According to other embodiments, a computer-implemented method for providing a personalized evaluation of CAD for a patient includes acquiring non-invasive images depicting the patient's coronary arteries and applying a machine learning model to a first set of features of interest extracted from the non-invasive images to yield a first prediction of coronary measures of interest. If the first prediction of coronary measures of interest indicates functionally significant CAD, then the patient is scheduled for invasive imaging of the patient's coronary arteries. In some embodiments, the method further includes acquiring invasive images depicting the patient's coronary arteries and applying the machine learning model to a second set of features of interest extracted from the invasive images to yield a second prediction of the coronary measures of interest. Then, the first prediction and the second prediction may be used to make one or more treatment decisions.

In other embodiments of the present invention, a computer-implemented method for providing a personalized evaluation of CAD for a patient includes acquiring one or more non-invasive images depicting the patient's coronary arteries and extracting a set of features of interest from the one or more non-invasive images. Invasive images depicting the patient's coronary arteries are also acquired. Then, a visualization may be provided which overlays the set of features of interest on the invasive images.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawing. For the purpose of illustrating the invention, there are shown in the drawing embodiments that are presently preferred, it being understood, however, that the invention is not limited to the specific instrumentalities disclosed. Included in the drawings are the following Figures:

FIG. 8 shows an example confusion matrix defined for CCTA-FFR and XA-FFR which may be utilized in some embodiments.

DETAILED DESCRIPTION

The following disclosure describes the present invention according to several embodiments directed at methods, systems, and apparatuses related to the personalized evaluation of coronary artery disease using an integration of multiple medical imaging techniques. Briefly, a first set of features is extracted from non-invasive medical imaging data of the coronary arteries of a patient. A trained machine learning model is used to predict a coronary measure of interest for each lesion in the coronary arterial tree. A second set of features is extracted from the invasive medical imaging data of the coronary arteries of a patient. The two sets of features are combined and the first set of features is used to provide corrections to features in the second set. Then, another trained machine learning model may be used to predict a coronary measure of interest for each lesion in the coronary arterial tree. This predicted coronary measures of interest can then be visualized in a graphical user interface (GUI). The techniques described herein may be applied to improve machine learning based prediction of coronary measure of interest, improve long-term outcome of the patient by a better identification of the true positive lesions, and simplify the invasive imaging procedure.

Figure 1:
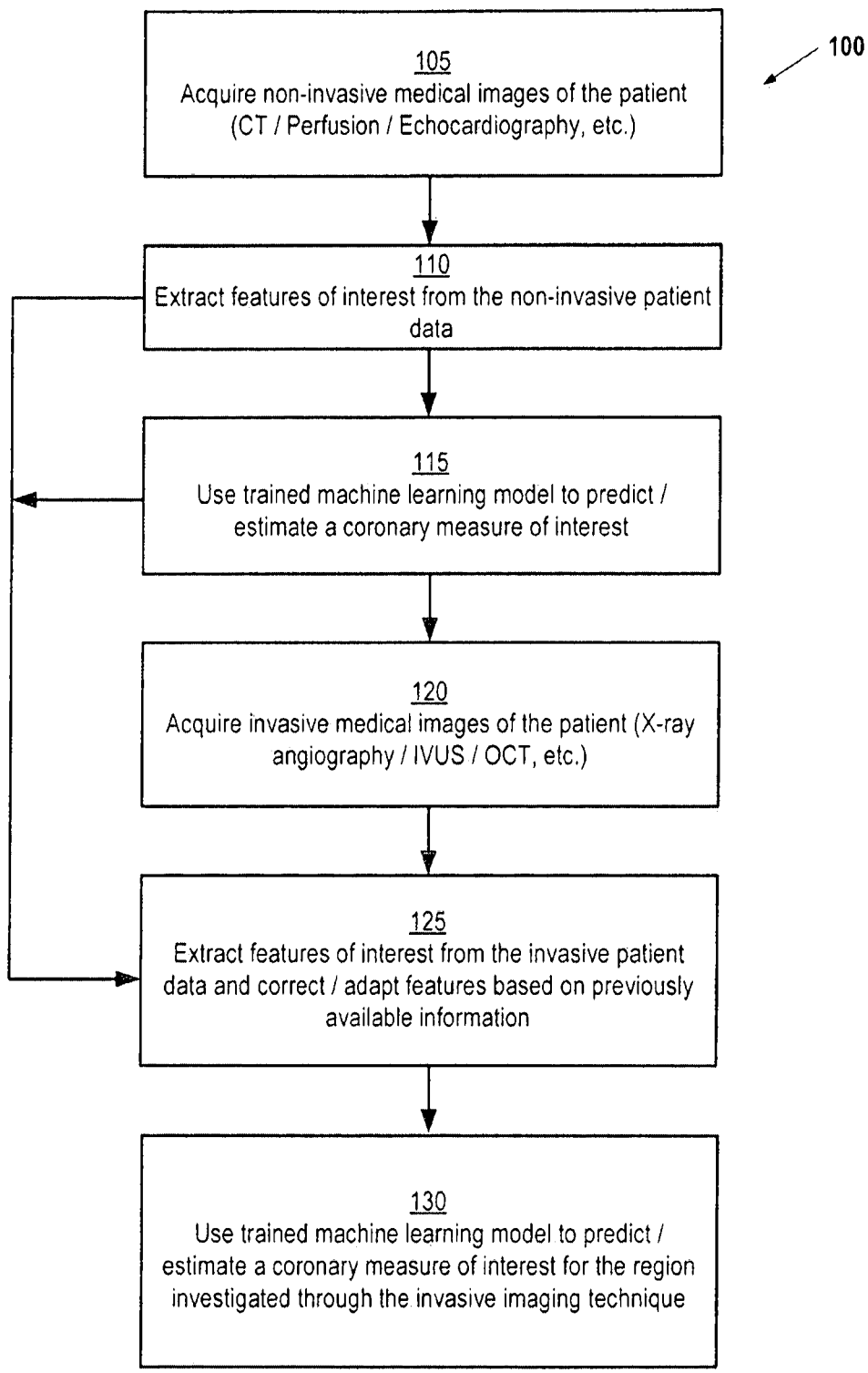
FIG. 1 displays the generic workflow applied in some embodiments to combine information extracted from multiple medical imaging techniques so as to provide machine learning (ML) based predictions of measures of interest for patients with CAD.

FIG. 1 displays the workflow 100 applied in some embodiments to combine information extracted from multiple medical imaging techniques so as to provide machine learning (ML) based predictions of measures of interest for patients with CAD. Herein we focus on the case where the first medical imaging technique is non-invasive and the second one is invasive. However, similar workflows may be defined for other combinations of medical imaging techniques, i.e., exclusively invasive or non-invasive techniques.

During step 105, a non-invasive medical imaging technique, like Coronary Computed Tomography Angiography (CCTA) is employed to acquire images depicting the anatomical information for the coronary arteries. Images acquired using non-invasive techniques are referred to herein as "non-invasive images." It should be noted that the term "acquire" as used in FIG. 1 and throughout this disclosure does not necessarily entail directly capturing the images at the imaging device; rather, in some embodiments, images are "acquired" by retrieving previously captured images from a storage medium.

Due to the tremendous improvement in medical imaging technologies, non-invasive imaging plays an increasingly important role in the diagnosis of CAD. CCTA is a non-invasive imaging modality which is being increasingly used for the visualization and diagnosis of CAD, prior to invasive catheterization. It should be noted that CCTA is only one example of the imaging technique that can be applied at step 105 and, in other embodiments, different non-invasive imaging techniques can be used.

Figure 2A:
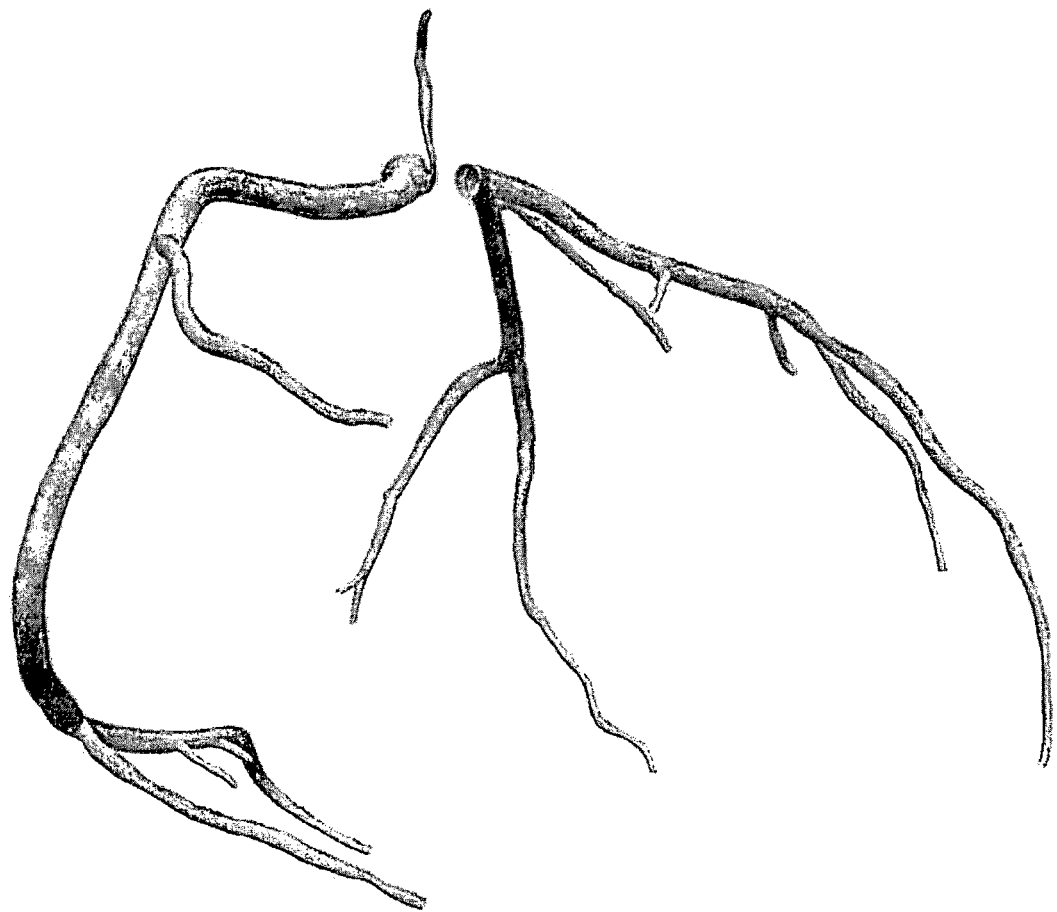
FIG. 2A shows an example of an anatomical model reconstructed from CCTA data.

Next, at step 110, a plurality of features of interest is extracted from the non-invasive patient data. These features may include, for example, lesions. The extraction of features may or may not involve the reconstruction of an anatomical model of the coronary arterial trees. For example, the features may be directly extracted from a medical image, or may be extracted from a geometric model that is built from medical image data. Techniques for reconstructing geometric models are generally known in the art and, thus, are not explained here in detail. FIG. 2A shows an example of an anatomical model reconstructed from CCTA data that may be used for feature extraction.

Continuing with reference to FIG. 1, at step 115, a machine learning model is applied to the features of interest to yield a prediction of one or more measures of interest at a certain location in the coronary arteries (e.g., downstream of a stenosis). This measure of interest may be FFR, but other measures like instantaneous wave-free ration (IFR), ratio of the resting distal pressure to the aortic pressure (rest Pd/Pa), basal stenosis resistance (BSR), hyperemic stenosis resistance (HSR), index of microcirculatory resistance (IMR) etc. may also be used. Examples of machine learning models that may be applied at step 115 include support vector machines (SVMs), standard neural networks, and convolutional neural networks. These models can be trained using datasets acquired from a large population to derive predictions based on features derived from the non-invasive data.

Subsequently, if there is an indication for a functionally significant stenosis, either based on anatomical information or on the prediction given by the machine learning model, the patient may be scheduled for an invasive medical imaging procedure, like X-ray Angiography (XA), to confirm the finding and eventually to also perform PCI (Percutaneous Coronary Intervention). The data acquired using an invasive medical imaging procedure is referred to herein as "invasive patient data" and the images are referred to as "invasive images." In FIG. 1, this invasive imaging is performed at step 120.

Figure 2B:
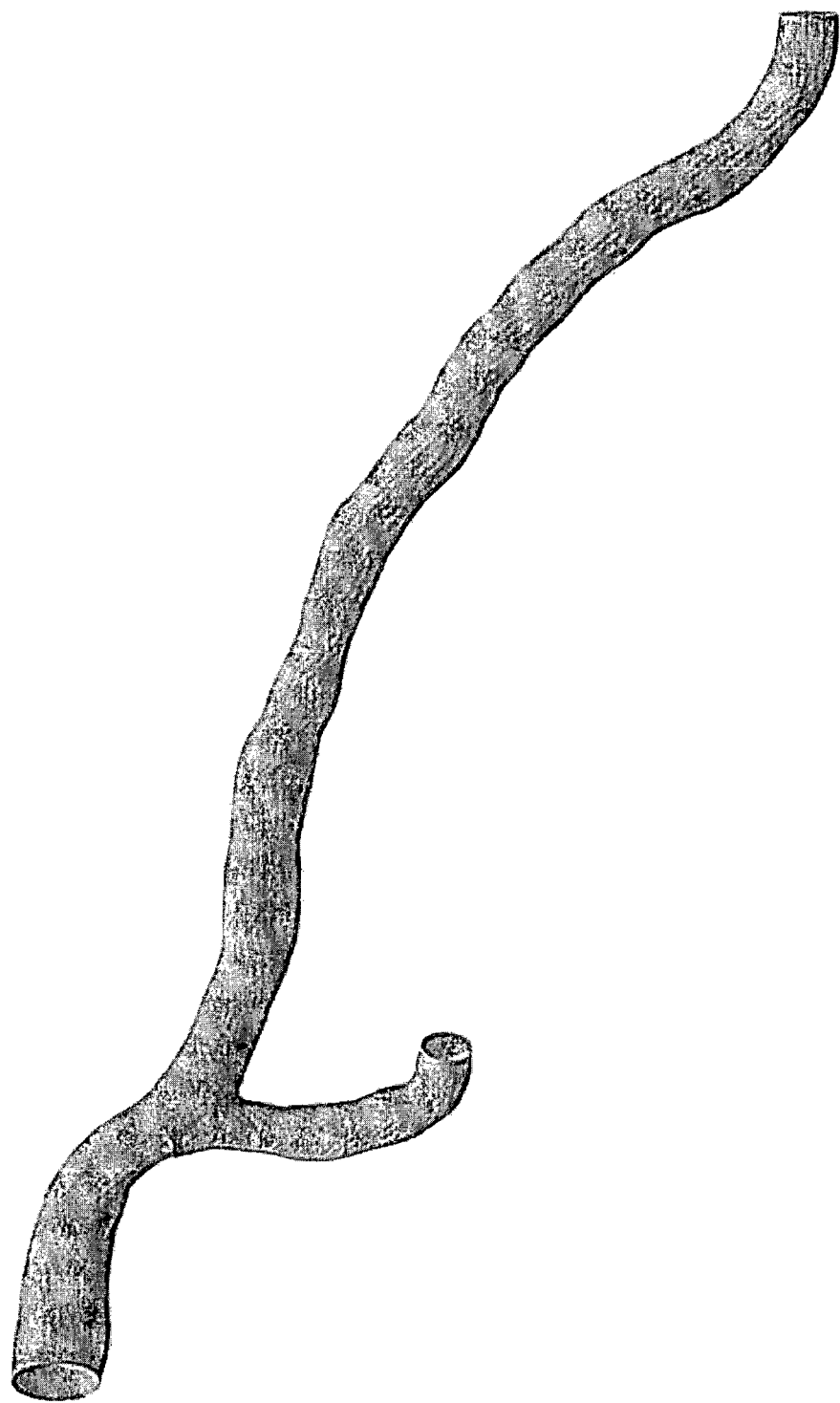
FIG. 2B shows an example of an anatomical model reconstructed from XA data.

Continuing with reference to FIG. 1, at step 125 features are extracted from the invasive patient data. The feature extraction techniques discussed above with respect to step 110 can be similarly applied at step 125. For example, in some embodiments, the features are extracted from a geometric model that is built from medical image data. FIG. 2B shows an example of an anatomical model reconstructed from XA data that may be used for feature extraction. Typically, the invasive imaging technique focuses on a certain region of interest in the coronary arteries. Thus, more accurate information related to that region of interest is obtained and the values of the features related to that region of interest are also more accurate. A crucial step in the workflow 100 is to combine this set of features which are related only to the region of interest, with the set of features extracted from the non-invasive medical imaging technique, which take into account the entire coronary circulation. Furthermore, in some embodiments, the measures of interest predicted based on the non-invasive medical imaging technique may also be used as additional feature.

At the last step of the workflow 100, at step 130, a second trained machine learning model is used to determine an "enhanced" prediction of the measure of interest based on the combined set of features generated based on the non-invasive and invasive imaging data. The term "enhanced prediction" is used herein to denote that this prediction enhances the prediction determined at step 115 by accounting for the entire coronary circulation. In some embodiments, the same machine learning model applied at step 115 can be applied at step 130. In other embodiments, different models can be applied for the non-invasive imaging data and the invasive imaging data. For example, the model required to process the non-invasive data can be computationally simpler and, thus, faster, than the model required to process the combined dataset. As such, the simpler machine learning model can be used at step 115 to determine an approximation that can then be refined, if necessary, with a more complex machine learning model at step 130.

In some embodiments, CCTA is the non-invasive medical imaging technique and XA is the invasive medical imaging technique. CCTA acquires volumetric data for the entire coronary circulation, and, hence, enables the generation of a complete coronary anatomical model, comprising all major arteries in the left and right tree as well as numerous side branches. FIG. 2 shows an example of an anatomical model reconstructed from CCTA data. Furthermore, the volumetric data may also be used to estimate the myocardial volume and mass. The extraction of features and the machine learning based prediction of coronary measures of interest, from invasive or non-invasive medical imaging data is described in further detail in United States Patent Application Publication No. 2016/0148371 to Itu et al., filed Jul. 21, 2015, entitled "SYNTHETIC DATA-DRIVEN HEMODYNAMIC DETERMINATION IN MEDICAL IMAGING" (hereinafter "the '371 application"), the entirety of which is incorporated herein by reference.

Figure 3:
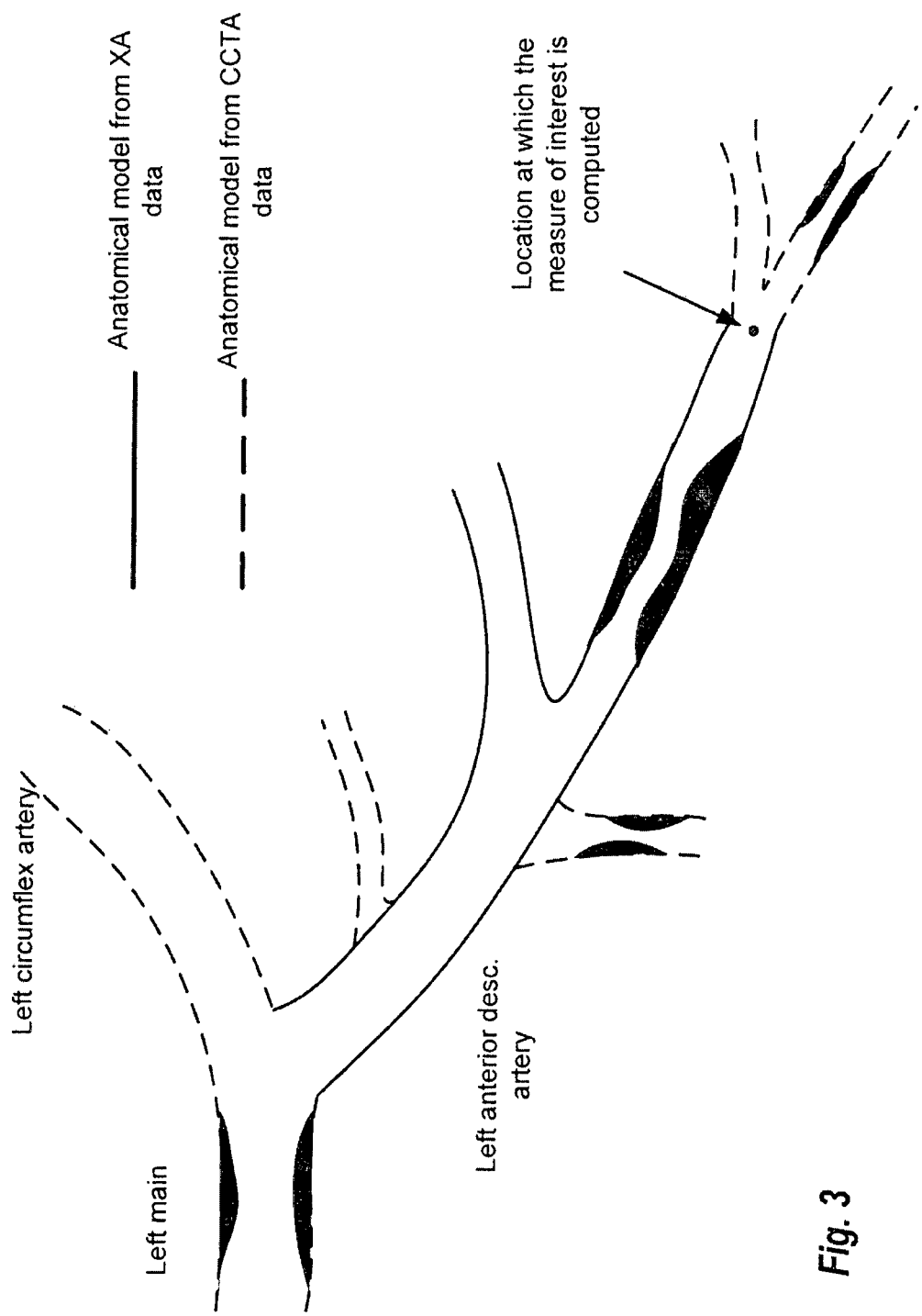
FIG. 3 shows a schematic representation of how information from one modality (here, prior CCTA) can be integrated with a different modality such as XA imaging.

As mentioned above, XA will provide more accurate information, but only for a certain region of interest. FIG. 3 shows an anatomical model of a coronary artery reconstructed from XA. This anatomical model may be complemented with information from CCTA. Specifically, the anatomical model may be extended with proximal arterial segments, side branches, and distal arterial segments. Hence, the values of the features used for the final machine learning based prediction become more accurate and allow for a better estimation of the measure of interest.

The '371 application describes two complex features related to the coronary arterial circulation (i.e., ischemic weight and ischemic contribution score). These two features are based on local and on global information of the coronary circulation. The ischemic weight is defined based on the radius information at all locations of an arterial tree. If the arterial tree is incomplete, as is the case for the anatomical models reconstructed exclusively from XA data, the ischemic weight values cannot be estimated reliably. For example, if a side branch is not present in the XA-based anatomical model (although XA has better resolution than CCTA, under certain conditions it may not be possible to reconstruct the side branch from XA data, for example, due to vessel overlap, foreshortening, etc.).

Furthermore, if proximal and distal segments reconstructed from CCTA are appended to the XA anatomical model, the additional radius information allows for a better estimation of the ischemic weight values. Because the ischemic weight is defined with a local-to global-to-local approach, the myocardial volume and the myocardial mass, extracted from CCTA data, may be used to correct the global ischemic weight defined at the second step of this approach. The ischemic contribution score is defined based on the ischemic weight and the radius information. Specifically the ischemic contribution score will be high in stenotic regions and low in healthy regions. CCTA data allows for a more comprehensive estimation of the ischemic weight; thus, this will also improve the estimation of the ischemic contribution score. Moreover, the presence of stenosis (which may be mild, moderate or severe) in the coronary segments which are reconstructed based on CCTA data and which complement the coronary segments reconstructed from XA, may have a significant effect on the final values of the ischemic contribution score.

FIG. 3 shows a schematic example of anatomical model of a coronary anatomical model reconstructed from XA data and complemented with information from CCTA data. This example has two mild stenosis in the proximal and distal segments, and a moderate stenosis in one of the side branches. The description for this figure should be something along the lines of "a schematic representation of how information from one modality (here, prior CCTA) can be integrated with a different modality such as XA imaging"

The values of the measure of interest derived from CCTA may also be used to modify the modus operandi of the XA procedure (reduce procedure time, reduce radiation, etc.). For example, if the right coronary artery (RCA) tree appears as being healthy on CCTA, it will not be imaged at all during the XA procedure. If only the left anterior descending (LAD) coronary artery appears to have lesions, the acquisition angles for the XA procedure may be predefined so as to have optimal views of the LAD and thus to minimize the number of series to be acquired and hence the radiation to the patient and operators. However, if one main branch has serial lesions whereas the most proximal one appears to be more severe than the others, the anatomical model reconstructed from XA data may contain only that specific lesion and the rest of the main branch may be taken over from CCTA data. This would be particularly important in case the reconstruction of the XA based anatomical models includes manual or semi-automatic steps, since this would be performed online during the XA procedure and would reduce the total procedure time.

Figure 4:
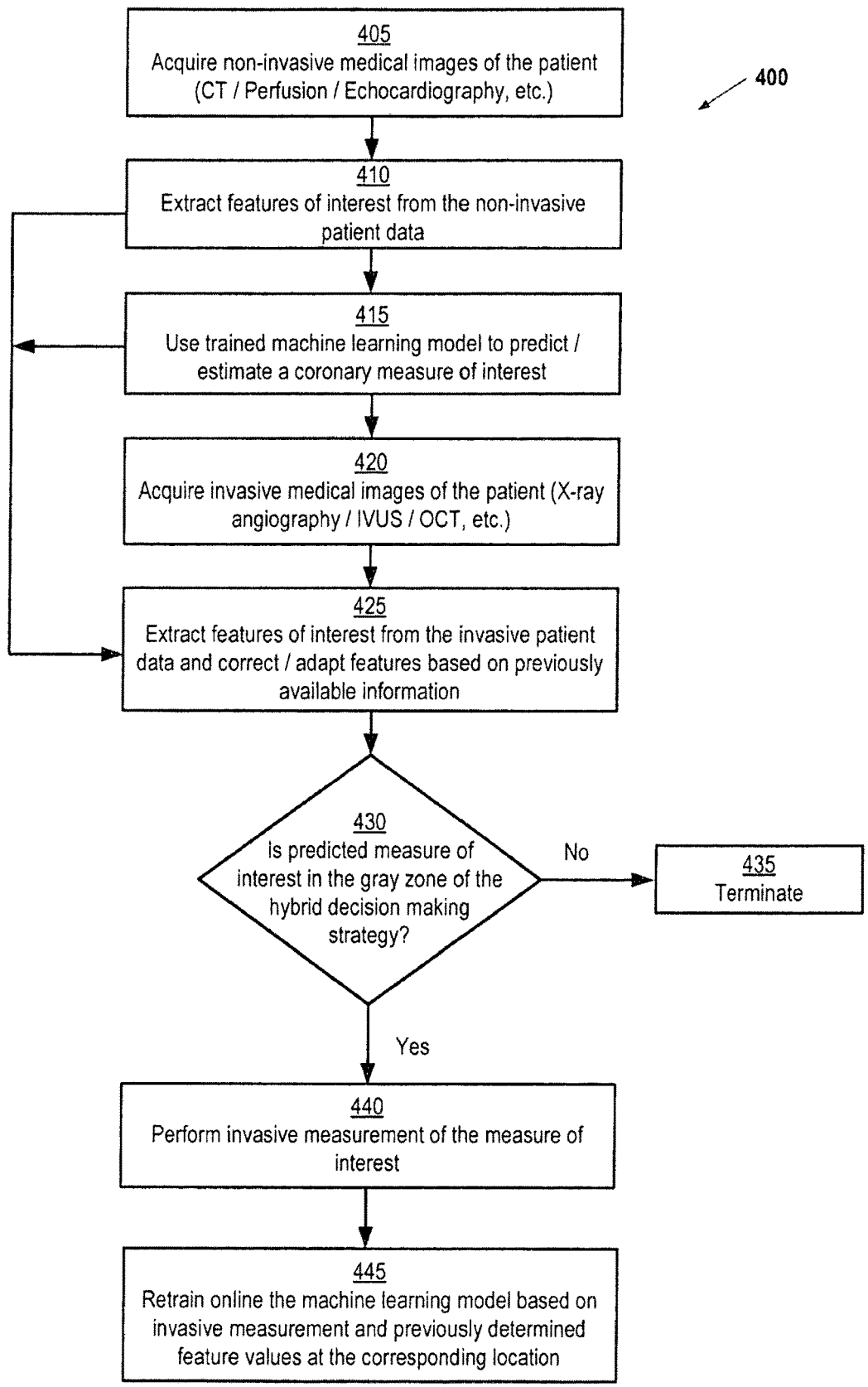
FIG. 4 shows a flow chart illustrating a workflow for performing an invasive pressure measurement in case a hybrid decision making strategy is employed, according to some embodiments.

In case an invasive measurement is performed (e.g. an invasive coronary pressure measurement for determining FFR) this information may be used to improve the trained machine learning model. FIG. 4 shows a flow chart illustrating a workflow 400 for performing an invasive pressure measurement in case a hybrid decision making strategy is employed, according to some embodiments. Steps 405-425 are largely the same as steps 105-125 of FIG. 1. Briefly, non-invasive medical imaging data is acquired at step 405 and a first set of features are extracted at step 410. At step 415, a machine learning model is used to predict a coronary measure of interest. Then, at step 420 invasive medical imaging data is acquired and, at step 425, a second set of features are extracted and combined with the first set of features. Using the combined set of features, an enhanced prediction of the coronary measure of interest is determined using the machine learning model.

Continuing with reference to FIG. 4, at step 430 the enhanced prediction of the measure of interest is evaluated to determine whether it is in the gray zone of the hybrid decision making strategy. The term "gray zone," as used herein, refers to the range of values for which, according to known studies, it is both safe to defer and treat stenosis. The term "hybrid decision making strategy" refers to a decision making process for functional assessment of coronary artery stenosis that considers both IFR and FFR measurements (hence the term "hybrid"). For example, in one embodiment, IFR>0.93 may be used to defer revascularization and IFR<0.86 may be used to confirm treatment. Lesions with intermediate IFR values between 0.93 and 0.86 (i.e., "gray zone" values") may be classified based on FFR. As an alternative to IFR, computed IFR (c-IFR) or computed FFR, derived from computational blood flow modeling and image-based anatomical reconstructions from routine coronary angiography may be used in some embodiments. The quantities used to defer revascularization and used to confirm treatment need not necessarily be the same.

If the predicted measure of interest is not in the gray zone, the workflow 400 terminates at step 435. However, if the predicted measure of interest is in the gray zone, the workflow 400 continues to 440 where invasive imaging or some other invasive measurement of the measurement of interest is used to acquire invasive measurement data. In this way, lesions for which the predicted measure of interest is close to the cut-off point are classified based on an invasive measurement. Next, at step 445, the machine learning model is retrained online based on the invasive measurement data and the feature values determined at step 425 so as to improve future predictions performed for similar lesions.

Figure 5:
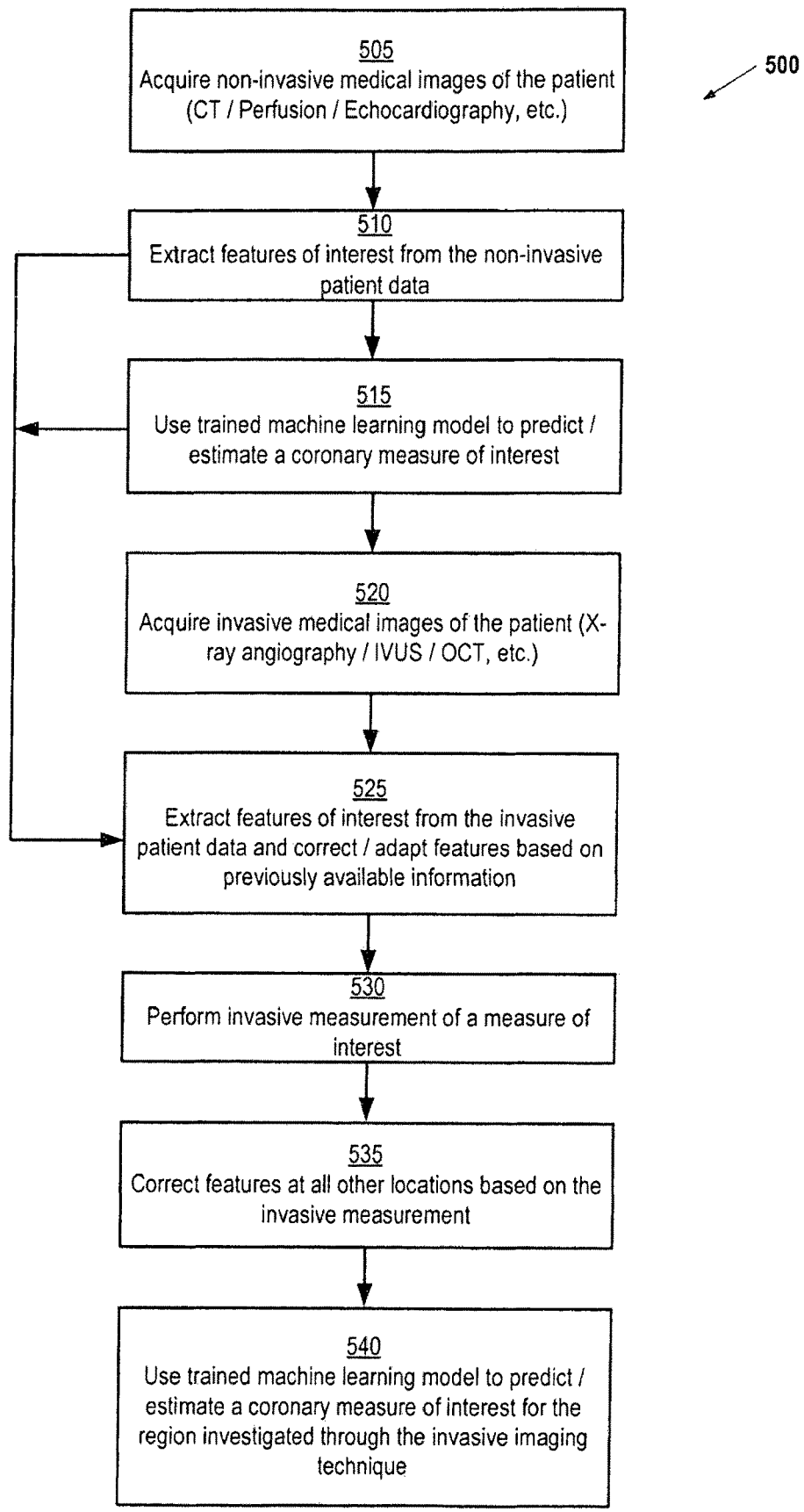
FIG. 5 shows an example workflow where the invasive measurement performed at one location may be used to correct features estimated at other locations so as to improve predictions at these locations, according to some embodiments.

Furthermore, the invasive measurement performed at one location may be used to correct features estimated at other locations so as to improve predictions at these locations as illustrated in the workflow 500 shown in FIG. 5. Steps 505-525 are similar to steps 105-125 of the workflow 100 shown in FIG. 1. Briefly, non-invasive medical imaging data is acquired at step 505 and a first set of features are extracted at step 510. At step 515, a machine learning model is used to estimate a coronary measure of interest. Then, at step 520 invasive medical imaging data is acquired and, at step 525, a second set of features are extracted and used to correct/adapt the first set of features. Various types of feature corrections may be applied at step 525. For example, as explained above, in some embodiments, the coronary artery segments reconstructed from invasive measurement data is incorporated into the complete coronary anatomical model reconstructed from non-invasive data. In other embodiments, the average radius of the healthy coronary segments determined via the invasive measurement data can be used to correct the corresponding features acquired or derived with the non-invasive measurement data.

Continuing with reference to FIG. 5, at step 530 an invasive measurement of the measure of interest is performed. In some embodiments, this invasive measurement is FFR or a similar guide wire-based procedure; although, in principle, any invasive coronary measurement may be acquired at step 530. At step 535, features at other locations on the coronary arterial tree are corrected based on the invasive measurement acquired at step 530. For example, the ischemic weights and/or ischemic contribution scores may be corrected as follows: if the measured quantity of interest indicates a more severe lesion than the machine learning based prediction, the value of the two features may be increased proportionally to the difference between measurement and prediction. For example:

$$w' = w + k_1(\text{FFR}_{ML} - \text{FFR}_{invasive}) \quad (1)$$

$$s' = s + k_2(\text{FFR}_{ML} - \text{FFR}_{invasive}) \quad (2)$$

where w and s are the initial values of the ischemic weight and the ischemic contribution score, w' and s' are the corrected values of the ischemic weight and the ischemic contribution score, $FFR_{ML}$ is the machine learning based prediction of the invasively measured $FFR_{invasive}$. The coefficients k1 and k2 are proportionality factors which may or may not be constant (for example they may be dependent on the distance between the location at which the invasive measurement was performed and the location at which the prediction is being corrected: $k=f(\Delta x)$.

More generally, eq. (1) and (2) may be rewritten as:

$$w'=f_1(w, FFR_{ML}, FFR_{invasive}) \quad (3)$$

$$s'=f_2(s, FFR_{ML}, FFR_{invasive}) \quad (4)$$

where $f_1$ and $f_2$ are mathematical operators. The invasive measurement may address a different quantity than the one predicted by the machine learning model. For example, FFR may be predicted by the ML model, and iFR, rest Pd/Pa or BSR may be measured invasively, i.e., during the rest state of the patient. This has the advantage that no hyperemia-inducing drug has to be administered and the risk of the procedure is reduced.

Once the features are corrected, at step 520, a machine learning model is used to estimate a coronary measure of interest for the region investigated through the invasive imaging technique. Another possibility is to employ a machine learning model to predict the measure of interest derived from the invasive imaging modality by using features and the measure of interest derived from the non-invasive imaging modality. This would basically provide a correction of the initial prediction. For example, in case of a high calcium score, it is expected that CCTA based predictions are biased towards values indicating positive lesions. By performing the correction, the bias would be eliminated and the prediction would be closer to the actual value of the lesion.

Enhanced therapy planning scenarios may also be defined for the CCTA and XA workflow. Generally, to assess the effect of each stenosis, and thus to determine which stenosis may require PCI/CABG, two approaches may be used. With the first approach, the user marks the stenosis to be treated; the geometry is modified so as to reflect the placement of a stent (whose size is chosen by the user) and the resulting change in geometry. With the second approach, stenoses are automatically detected and the algorithm used for assessing the hemodynamic metrics is adapted so as to remove the effect of the stenosis on the hemodynamics (in this case the initial geometry does not have to be modified). Although straight-forward from an algorithmic point of view, the first approach has the disadvantage that it relies on extensive user interaction: the stenosis is identified, a stent size is chosen, the effect of stent placement on the geometry is assessed, etc. The second approach is fully automated and the user only needs to select the stenosis whose effect on the hemodynamic metric needs to be assessed.

For the second approach, one method would comprise modifying the features related to the ischemic weights and ischemic contribution scores of the stenotic segments. This approach could be even further extended in the sense that all possible post-stenting scenarios may be evaluated and a comprehensive analysis may be displayed to the user, where the stenoses are ranked based on their effect on the hemodynamic metrics. A suggestion is given to the user regarding the stenoses which require treatment. In the combined CCTA and XA workflow, the therapy planning step may be performed after acquiring the CCTA data. Since this acquisition is noninvasive, the user/clinician would have more to time to experiment and test out different scenarios than during the invasive XA procedure. Stent sizes, lengths, etc. may be preliminarily decided at this time and then only confirmed or marginally corrected during the XA procedure. An algorithm may also be used to automatically correct the therapy planning choices during the XA procedure, based on anatomical differences between the vessel characteristics extracted from CCTA and XA data.

The therapy planning step can also be performed at time of the XA procedure, especially if it requires minimal user interaction. The therapy planning step also profits from the integration of CCTA and XA, as described above, since the input data required for this step is much more comprehensive.

Separate machine learning models may additionally be used to provide a confidence interval for the estimation of the measure of interest (based on uncertainty quantification analysis). For this, in one embodiment, the first step would be to use a set of uncertain input variables in the training data, propagate this uncertainty through the forward model and determine the uncertainty for the hemodynamic metric. The uncertainty can then be learned through a machine learning model based on the extracted features. The same features are then extracted for a patient-specific geometry and uncertainty in the input data is specified either automatically or by the user, and using the ML algorithm the confidence of the estimated hemodynamic metric is provided.

The uncertainty analysis may be performed based on the CCTA data, and may indicate regions in the coronary geometry where the measure of interest is particularly sensitive with respect to the anatomical information. This information may then be used for indicating which regions should be targeted for the XA procedure, so as to enhance the confidence in the predicted measures of interest. Of course, the uncertainty analysis may also be performed based on the XA data and thus indicate regions of interest on which the user/clinician should focus for the semi-automatic/manual steps (e.g. correction of segmentation).

In the workflows described above, CCTA data is used to enhance the features extracted from XA data and, thus, to improve the corresponding machine learning based prediction of measures of interest. Conversely, the XA information may in turn be used to correct the initial predictions which were performed based on features extracted from CCTA data.

Figure 6:
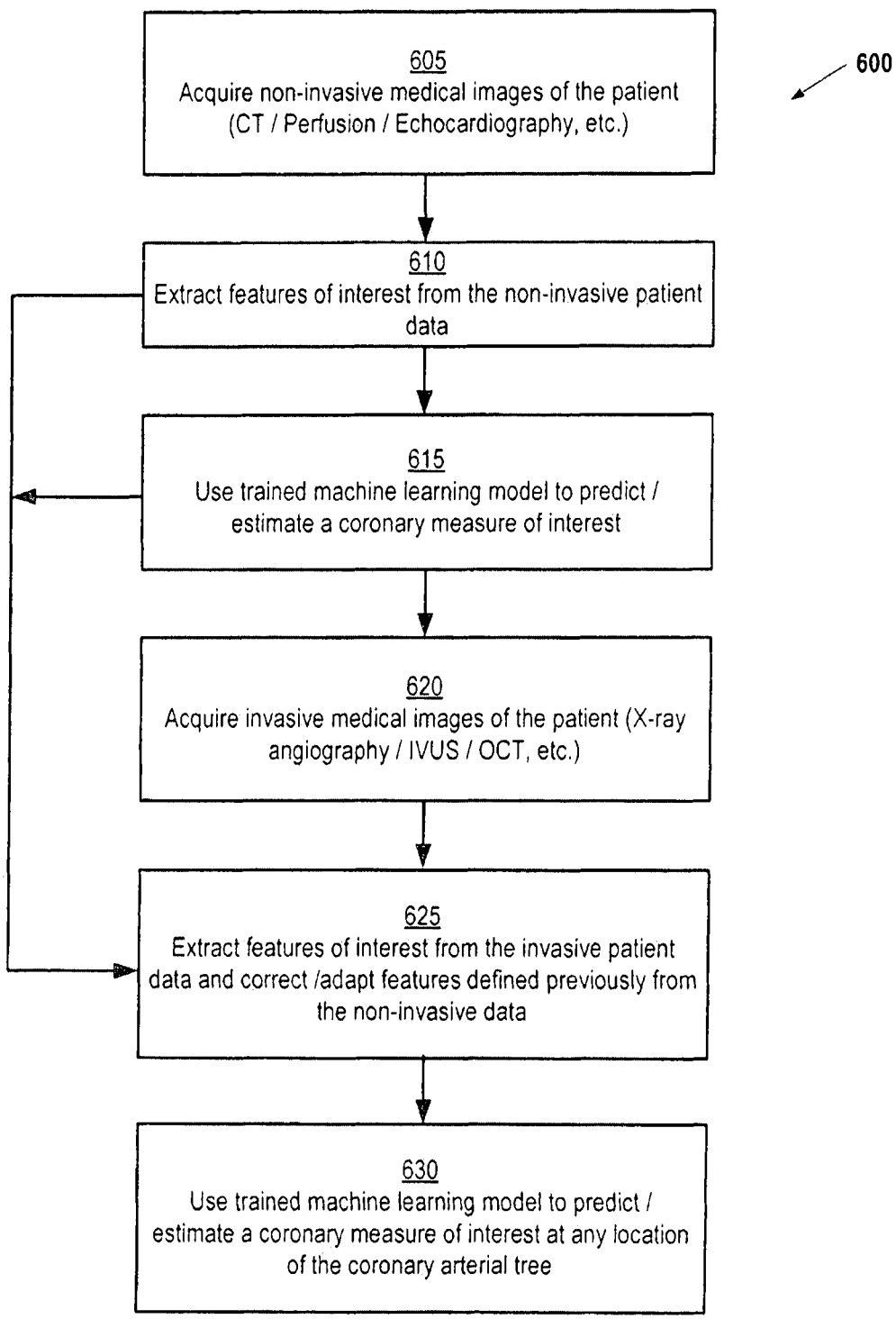
FIG. 6 provides a flowchart illustrating a workflow for correcting a machine learning based prediction performed on features extracted from noninvasive medical imaging data by embedding information from invasive medical imaging data, according to some embodiments.

FIG. 6 provides a flowchart illustrating a workflow 600 for correcting a machine learning based prediction performed on features extracted from noninvasive medical imaging data by embedding information from invasive medical imaging data, according to some embodiments. In steps 605 and 610, non-invasive medical images are acquired and features are extracted from those images. Next, at step 615, a machine learning model is used to predict a coronary measure of interest. Invasive medical images of the patient are acquired at 620 and, at step 625, features of interest are extracted from the invasive images. These features are then used to correct/adapt features defined previously from the non-invasive imaging data. Finally, at step 630, a machine learning model is used to predict a coronary measure of interest at any location of the coronary arterial tree.

Various approaches may be used for correcting the features defined from CCTA data based on features extracted from XA data. For example, in the coronary circulation there is a strong interdependency between different coronary segments on different branches. This is also reflected by the methods used to define the features in an ML based workflow for predicting coronary measures of interest (as described in the '371 application). Thus, one approach to feature correction is to embed the coronary artery segments reconstructed from XA data into the complete coronary anatomical model reconstructed from CCTA data. This will lead to a change in the feature values at all locations, and, hence, also lead to modified predictions of the measure of interest at all locations of interest. Since the ML based predictions can be performed in real time during the XA procedure, this may have an effect on the XA procedure itself. Let's consider the following situation: two stenosis are identified as being functionally significant when applying the ML model for features extracted exclusively from CCTA data, one in the LAD and one in the LCx. During the XA procedure the LAD lesion is first examined. Once the features have been extracted from XA data and used to correct the features for the entire coronary tree, the new prediction performed for the LCx lesion may indicate that it is functionally not significant and hence that it no longer has to be investigated through XA and/or treated invasively through PCI.

The anatomical model reconstructed from XA data may have different global properties than the same coronary region reconstructed from CCTA data. For example the average radius of the healthy coronary segments may be, on average, larger or smaller than the average radius in the CCTA based reconstruction. This information may be used as a second approach to feature correction to the CCTA based reconstructions at all locations, which in turn will affect the features and the ML based predictions. The first two approaches to feature correction discussed above may also be used if no anatomical models are reconstructed, i.e., the features are extracted directly from the imaging data. As a third alternative approach to feature correction, contrast propagation information (bolus transit time, bolus velocity, etc.) may be used to correct certain features like the ischemic weight, ischemic contribution score, etc.

Enhanced therapy planning scenarios may also be defined if the focus lies on the CCTA data. For example a virtual PCI may be performed on a branch which was not visualized with XA, and this may influence the prediction on the branch visualized through XA and integrated in the CCTA data. This would for example be the case if the former contains a severe stenosis which very likely requires PCI. Furthermore, if a lesion was stented during the invasive XA procedure, the post-stenting geometry may be integrated into the CCTA data so as to be able to provide an enhanced prediction for the other branches/lesions in the post-stenting scenario.

Figure 7:
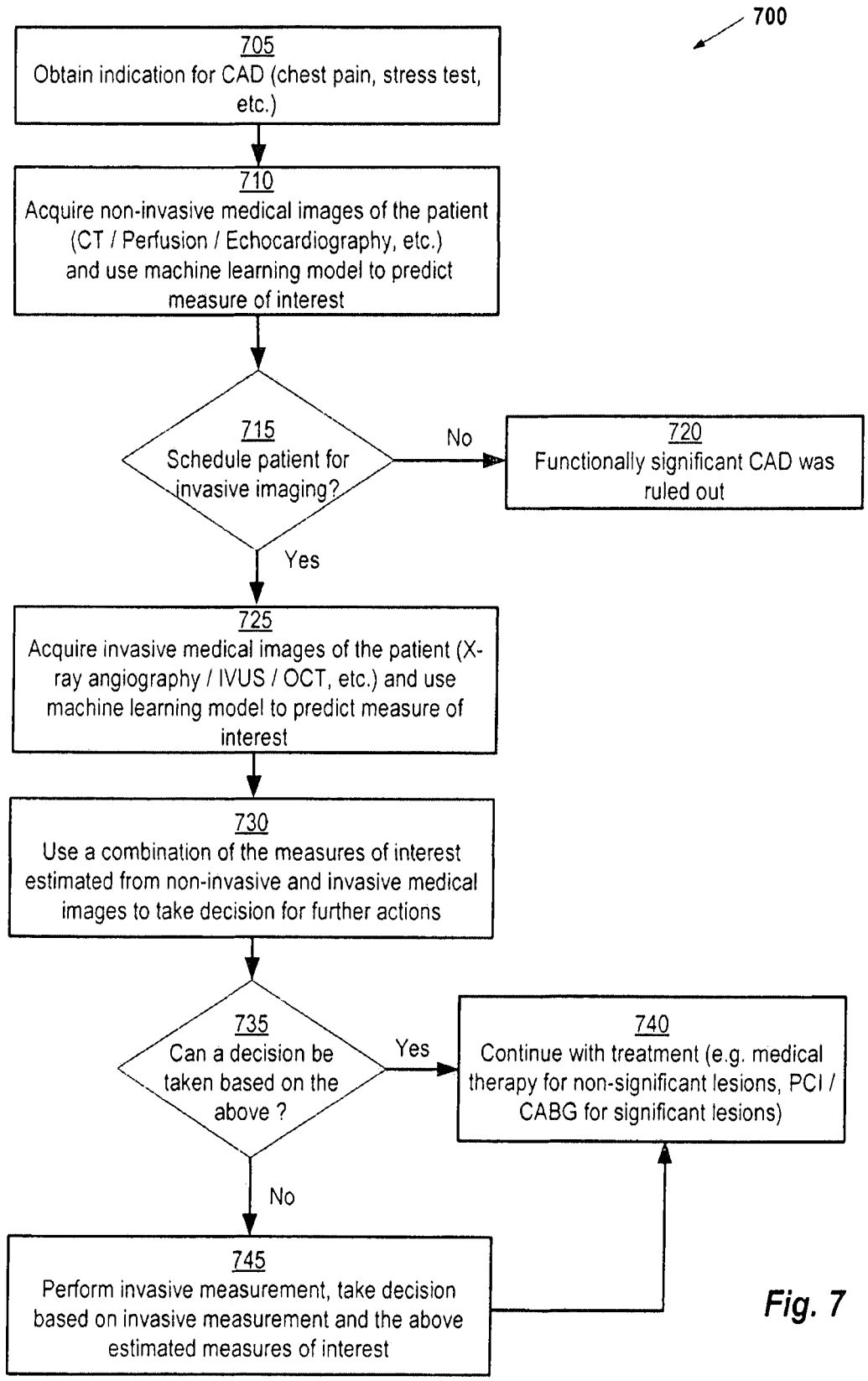
FIG. 7 displays a generic version of a clinical workflow, according to some embodiments.

FIG. 7 displays a generic version of a clinical workflow 700, which is based on the methodologies described in the previous sections. In this workflow 700, first an indication for CAD is established at step 705. This may be done, for example, based on the chest pain reported by the patient, a stress test, etc. Next, at step 710 a non-invasive imaging method like CCTA is employed to obtain a first confirmation for CAD. The usage of CCTA as gatekeeper in the diagnosis of CAD is generally understood by those skilled in the art. Hence, CCTA may be used to decrease the number of invasive diagnosis procedures (i.e., angiography exams, during which no significant CAD is found). Functional measures of interest derived from CCTA have been shown to be superior to anatomical markers. Such features can be extracted and a machine learning model can be applied to those features to predict a measure of interest.

This measure of interest derived at step 710 is used at step 715 to determine whether to schedule the patient for invasive imaging at a catheterization laboratory. If this measure of interest indicates functionally non-significant CAD, invasive imaging is not performed and the patient may be treated with medical therapy alone. If there is an indication for functionally significant CAD, invasive imaging of the patient is performed at step 725.

Continuing with reference to FIG. 7, at step 730, a combination of the measures of interest estimated from the non-invasive and invasive medical images are used to determine whether additional actions should be performed. Different thresholds may be used for the measure of interest derived from different imaging modalities in the decision making process. For the non-invasive imaging modality, the threshold for the ML based measure of interest may be biased towards a higher sensitivity, so as to minimize the number of false negatives. This may lead to a decrease of the specificity, but the risk of ruling out functionally significant CAD is minimized. This result may also be achieved by maintaining the threshold constant, but biasing the values of one more feature towards a more severe lesion. For the invasive imaging modality, the threshold for the ML based measure of interest ($MeasInt_{inv}$) may be biased as a function of the ML based measure of interest derived from the non-invasive imaging modality ($MeasInt_{non-inv}$). For example, if $MeasInt_{non-inv}$ indicates a negative lesion, the threshold of $MeasInt_{inv}$ may be biased towards having fewer positive lesions: the lesion is expected to be negative, thus it will be marked as being positive only if $MeasInt_{inv}$ indicates a positive lesion with the more challenging threshold. Conversely, if $MeasInt_{non-inv}$ indicates a positive lesion, the threshold of $MeasInt_{inv}$ may be biased towards having fewer negative lesions: the lesion is expected to be positive, thus it will be marked as being negative only if $MeasInt_{inv}$ indicates a negative lesion with the more challenging threshold.

The aforementioned point can be similarly applied in case a hybrid decision making strategy is employed, which involves invasive measurements. To simplify the explanation we will refer to FFR as being the measure of interest. The hybrid strategy refers in this case to XA-FFR (ML based prediction of FFR from XA medical data) (i.e., if the value of XA-FFR lies in a gray zone area defined around the cut-off of 0.8, the decision is taken based on the invasively measured value). In this case if CCTA-FFR (ML based prediction of FFR from CCTA medical data) is positive, the lower threshold of the hybrid window for XA-FFR may be increased, thus strengthening the confidence of a positive lesion detection. If CCTA-FFR is negative, the upper threshold of the hybrid window for XA-FFR may be decreased, thus strengthening the confidence of a negative lesion detection. In some embodiments, the confusion matrix shown in FIG. 8 may be used, which is defined for CCTA-FFR and XA-FFR, but which may be defined in a similar way for other measures of interest. Each of the four cells contains information regarding the decision taken for a lesion once CCTA-FFR and XA-FFR have been determined.

In some embodiments, the threshold of the invasively measured quantity of interest at step 725 may also be modified based on the ML based predictions. It is known that invasive measurements have an inherent variability and uncertainty. Furthermore, a weighted sum of both ML based predictions and of invasive measurements may be used to take the final decision regarding the treatment of the patient.

Next, at step 735, all of the previously acquired information, including the values of the measures of interest derived from noninvasive and invasive medical images is employed for making a decision regarding the next step. The exact decision made in step 735 can vary depending on the treatment plan. For example, this decision can be whether medical therapy should be performed in case of non-significant lesions or Percutaneous Coronary Intervention (PCI) or Coronary Artery Bypass Grafting (CABG) in the case of significant lesions If the amount of information gathered suffices to make a decision regarding the treatment, the treatment continues at step 740 based on the targeted area of interest. Alternately, if the amount of information gathered does not suffice, invasive measurements are performed at step 745 and taken into account when deciding the treatment plan for the patient at step 740. This corresponds to a hybrid decision-making strategy, whereas, for lesions lying in a gray zone area, the decision is taken based on an invasive measurement.

In some embodiments of the workflow shown in FIG. 7, a weighted sum of the ML based measure of interest predictions from CCTA and XA may be used when deciding the treatment plan for the patient. Patient-specific weights may be used, which may be dependent on the image quality of the modality, the time interval between the two measurements, the number of branches reconstructed from CCTA, the size of branches, the size of the region of interest imaged through XA, the values of features (e.g. based on the number of data sets with similar feature values in the training set), etc.

As an additional application of the techniques described herein, in some embodiments, different features (e.g., lesions, computed FFR, etc.) from the non-invasive images are combined with the live view of the invasive images. This combination provides a fusion of the functional or anatomical quantities from the non-invasive images with the invasive ones. Thus, for example, in some embodiments, non-invasive images depicting the patient's coronary arteries are acquired and a set of features of interest are extracted from the one or more non-invasive images. A visualization may then be provided by overlaying the features onto the invasive images. Techniques for overlaying visualized 3D structures onto images are described generally in U.S. Pat. No. 8,494,245 to Liao et al., issued Jul. 23, 2013, entitled "System and method for guiding transcatheter aortic valve implantations based on interventional C-Arm CT imaging," the entirety of which is incorporated herein by reference.

Figure 9:
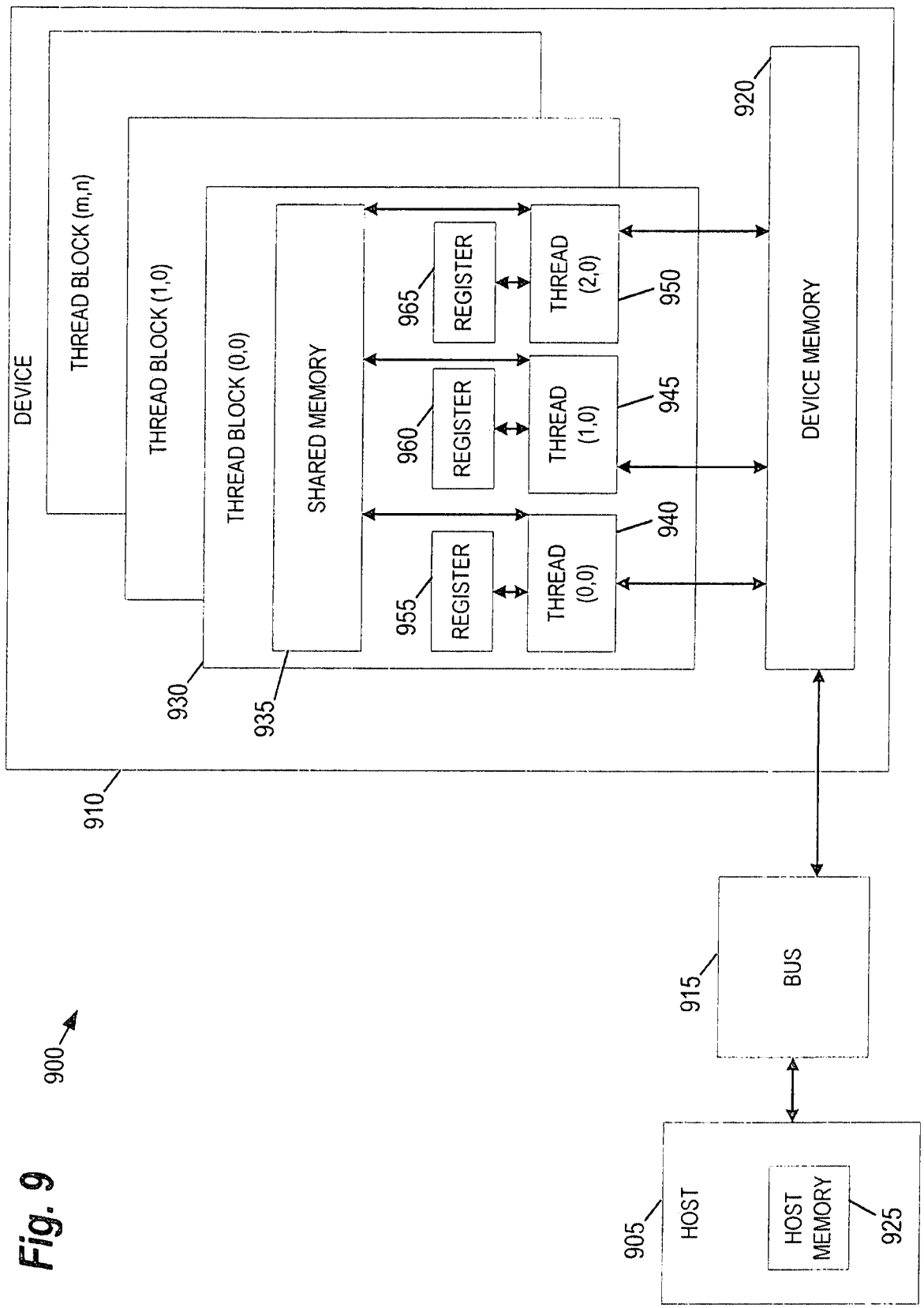
FIG. 9 provides an example of a parallel processing memory architecture that may be utilized to implement the machine learning models and other aspects of the various workflows discussed herein.

FIG. 9 provides an example of a parallel processing memory architecture 900 that may be utilized to implement the machine learning models and other aspects of the various workflows discussed herein. This architecture 900 may be used in embodiments of the present invention where NVIDIA CUDA™ (or a similar parallel computing platform) is used. The architecture includes a host computing unit ("host") 905 and a graphics processing unit (GPU) device ("device") 910 connected via a bus 915 (e.g., a PCIe bus). The host 905 includes the central processing unit, or "CPU" (not shown in FIG. 9), and host memory 925 accessible to the CPU. The device 910 includes the graphics processing unit (GPU) and its associated memory 920, referred to herein as device memory. The device memory 920 may include various types of memory, each optimized for different memory usages. For example, in some embodiments, the device memory includes global memory, constant memory, and texture memory.

Parallel portions of a big data platform and/or big simulation platform (see FIG. 9) may be executed on the architecture 900 as "device kernels" or simply "kernels." A kernel comprises parameterized code configured to perform a particular function. The parallel computing platform is configured to execute these kernels in an optimal manner across the architecture 900 based on parameters, settings, and other selections provided by the user. Additionally, in some embodiments, the parallel computing platform may include additional functionality to allow for automatic processing of kernels in an optimal manner with minimal input provided by the user.

The processing required for each kernel is performed by a grid of thread blocks (described in greater detail below). Using concurrent kernel execution, streams, and synchronization with lightweight events, the architecture 900 of FIG. 9 (or similar architectures) may be used to parallelize portions of the model based operations performed in training or utilizing the workflows discussed herein. For example, in embodiments where a convolutional neural network is used as the machine learning model, the architecture 900 can be used to perform operations such as forward and backward convolution, pooling, normalization, etc. with the non-invasive and invasive images.

The device 910 includes one or more thread blocks 930 which represent the computation unit of the device 910. The term thread block refers to a group of threads that can cooperate via shared memory and synchronize their execution to coordinate memory accesses. For example, in FIG. 9, threads 940, 945 and 950 operate in thread block 930 and access shared memory 935. Depending on the parallel computing platform used, thread blocks may be organized in a grid structure. A computation or series of computations may then be mapped onto this grid. For example, in embodiments utilizing CUDA, computations may be mapped on one-, two-, or three-dimensional grids. Each grid contains multiple thread blocks, and each thread block contains multiple threads. For example, in FIG. 9, the thread blocks 930 are organized in a two dimensional grid structure with m+1 rows and n+1 columns. Generally, threads in different thread blocks of the same grid cannot communicate or synchronize with each other. However, thread blocks in the same grid can run on the same multiprocessor within the GPU at the same time. The number of threads in each thread block may be limited by hardware or software constraints.

Continuing with reference to FIG. 9, registers 955, 960, and 965 represent the fast memory available to thread block 930. Each register is only accessible by a single thread. Thus, for example, register 955 may only be accessed by thread 940. Conversely, shared memory is allocated per thread block, so all threads in the block have access to the same shared memory. Thus, shared memory 935 is designed to be accessed, in parallel, by each thread 940, 945, and 950 in thread block 930. Threads can access data in shared memory 935 loaded from device memory 920 by other threads within the same thread block (e.g., thread block 930). The device memory 920 is accessed by all blocks of the grid and may be implemented using, for example, Dynamic Random-Access Memory (DRAM).

Each thread can have one or more levels of memory access. For example, in the architecture 900 of FIG. 9, each thread may have three levels of memory access. First, each thread 940, 945, 950, can read and write to its corresponding registers 955, 960, and 965. Registers provide the fastest memory access to threads because there are no synchronization issues and the register is generally located close to a multiprocessor executing the thread. Second, each thread 940, 945, 950 in thread block 930, may read and write data to the shared memory 935 corresponding to that block 930. Generally, the time required for a thread to access shared memory exceeds that of register access due to the need to synchronize access among all the threads in the thread block. However, like the registers in the thread block, the shared memory is typically located close to the multiprocessor executing the threads. The third level of memory access allows all threads on the device 910 to read and/or write to the device memory. Device memory requires the longest time to access because access must be synchronized across the thread blocks operating on the device. Thus, in some embodiments, an image can be divided into segments using data locality techniques generally known in the art. Then, each segment can be processed in parallel using register memory, with shared and device memory only being used as necessary to combine the results to provide the results for the complete image.

The embodiments of the present disclosure may be implemented with any combination of hardware and software. For example, aside from parallel processing architecture presented in FIG. 9, standard computing platforms (e.g., servers, desktop computer, etc.) may be specially configured to perform the techniques discussed herein. In addition, the embodiments of the present disclosure may be included in an article of manufacture (e.g., one or more computer program products) having, for example, computer-readable, non-transitory media. The media may have embodied therein computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

The invention claimed is:

1. A method for providing a personalized evaluation of coronary artery disease (CAD) for a patient, the method comprising:
    acquiring one or more non-invasive images depicting a patient's coronary arteries;
    extracting a first set of features of interest from the one or more non-invasive images;
    applying a first machine learning model to the first set of features of interest to yield a prediction of one or more coronary measures of interest at a certain location in the coronary arteries;
    acquiring one or more invasive images depicting the patient's coronary arteries, wherein the invasive images depict regions of interest selected based on the prediction of one or more coronary measures of interest;
    extracting a second set of features of interest from the one or more invasive images;
    combining the first set of features of interest and the second set of features of interest to yield a combined set of features of interest; and
    applying a second machine learning model to the combined set of features of interest to yield an enhanced prediction of the one or more coronary measures of interest accounting for full coronary circulation.

2. The method of claim 1, wherein the non-invasive images comprise Computed Tomography Angiography (CCTA) images and the invasive images comprise X-ray Angiography (XA) images.

3. The method of claim 1, wherein the combined set of features of interest further includes the prediction of the one or more coronary measures of interest.

4. The method of claim 1, wherein the first set of features are extracted directly from the one or more non-invasive images.

5. The method of claim 1, further comprising:
    generating a geometric model of the patient's coronary arteries using the one or more non-invasive images,
    wherein the plurality of features are extracted from the geometric model.

6. The method of claim 1, wherein the one or more coronary measures of interest comprise a measurement of Fractional Flow Reserve (FFR).

7. The method of claim 1, wherein the one or more coronary measures of interest comprise a measurement of one or more of instantaneous wave-free ratio (IFR), ratio of resting distal pressure to aortic pressure (rest Pd/Pa), basal stenosis resistance (BSR), hyperemic stenosis resistance (HSR), and index of microcirculatory resistance (IMR).

8. The method of claim 1, further comprising:
determining whether the enhanced prediction of the one or more coronary measures of interest is in a gray zone of a hybrid decision making strategy; and
if the one or more coronary measures of interest is in the gray zone of the hybrid decision making strategy, performing an invasive measurement of the one or more coronary measures of interest to acquire invasive measurement data.

9. The method of claim 8, further comprising:
retraining the machine learning model based on the invasive measurement data and the combined set of features of interest.

10. The method of claim 8, wherein the hybrid decision making strategy is based on a decision of performing iFR measurements or FFR measurements.

11. The method of claim 8, wherein the invasive measurement is an FFR measurement.

12. A computer-implemented method for providing a personalized evaluation of CAD for a patient, the method comprising:
acquiring one or more non-invasive images depicting a patient's coronary arteries;
extracting a first set of features of interest from the one or more non-invasive images;
applying a first machine learning model to the first set of features of interest to yield a prediction of one or more coronary measures of interest at a certain location in the coronary arteries;
acquiring one or more invasive images depicting the patient's coronary arteries, wherein the invasive images depict regions of interest selected based on the prediction of one or more coronary measures of interest;
extracting a second set of features of interest from the one or more invasive images; and
performing (i) a correction of at least a portion of the first set of features of interest using the second set of features of interest or (ii) a correction of at least a portion of the second set of features of interest using the first set of features of interest to yield a corrected set of features of interest;
applying a second machine learning model to the corrected set of features of interest to yield an updated prediction of the one or more coronary measures of interest accounting for full coronary circulation.

13. The method of claim 12, further comprising:
acquiring an invasive measurement of the one or more coronary measures of interest; and
performing additional corrections on the corrected set of features of interest based on the invasive measurement.

14. The method of claim 12, wherein the non-invasive images comprise CCTA images and the invasive images comprise XA images.

15. The method of claim 12, wherein the first set of features of interest includes the prediction of the one or more coronary measures of interest.

16. A computer-implemented method for providing a personalized evaluation of CAD for a patient, the method comprising:
acquiring one or more non-invasive images depicting the patient's coronary arteries;
applying a first machine learning model to a first set of features of interest extracted from the one or more non-invasive images to yield a first prediction of one or more coronary measures of interest at a certain location in the coronary arteries;
determining whether the first prediction of the one or more coronary measures of interest indicates functionally significant CAD; and
if the first prediction of coronary measures of interest indicates functionally significant CAD, then scheduling the patient for invasive imaging of the patient's coronary arteries;
acquiring one or more invasive images depicting the patient's coronary arteries, wherein the invasive images depict regions of interest selected based on the prediction of one or more coronary measures of interest; and
applying a second machine learning model to a second set of features of interest extracted from the one or more invasive images to yield a second prediction of the one or more coronary measures of interest accounting for full coronary circulation.

17. The method of claim 16, further comprising:
using the first prediction and the second prediction of the one or more coronary measures of interest to make one or more treatment decisions.

18. The method of claim 16, wherein the non-invasive images comprise CCTA images and the invasive images comprise XA images.

* * * * *